US006599523B2

(12) United States Patent
Cohen et al.

(10) Patent No.: US 6,599,523 B2
(45) Date of Patent: *Jul. 29, 2003

(54) PREPARATION OF PEROXIDE-OXIDIZED, SULFONATED, AND PHOSPHORYLATED COTTON

(75) Inventors: Kelman I. Cohen, Richmond, VA (US); Robert F. Diegelmann, Richmond, VA (US); Dorne Yager, Chesterfield, VA (US); Judson Vincent Edwards, Mandeville, LA (US)

(73) Assignees: Virginia Commonwealth University, Richmond, VA (US); The United States of America as represented by the Department of Agriculture, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/794,227

(22) Filed: Feb. 28, 2001

(65) Prior Publication Data

US 2002/0012693 A1 Jan. 31, 2002

Related U.S. Application Data

(63) Continuation-in-part of application No. 09/515,172, filed on Feb. 29, 2000.

(51) Int. Cl.[7] .......................... A61F 13/00; A61L 15/00
(52) U.S. Cl. ................. 424/443; 424/445; 424/446; 424/447; 424/449; 602/41; 602/42; 602/43; 602/48; 602/49
(58) Field of Search ................. 424/443, 449; 602/41, 42, 48

(56) References Cited

U.S. PATENT DOCUMENTS

| 4,453,939 | A |   | 6/1984 | Zimmerman et al. ........ 604/368 |
| 5,098,417 | A |   | 3/1992 | Yamzaki et al. ............ 604/304 |
| 5,187,153 | A |   | 2/1993 | Cordell et al. .................. 514/12 |
| 5,696,101 | A |   | 12/1997 | Wu et al. ....................... 514/57 |
| 5,705,177 | A |   | 1/1998 | Roufa et al. ................... 424/22 |
| 5,705,178 | A |   | 1/1998 | Roufa et al. ................... 514/59 |
| 5,733,563 | A | * | 3/1998 | Fortier ......................... 424/422 |
| 5,773,430 | A |   | 6/1998 | Simon et al. ................. 514/152 |
| 5,807,555 | A |   | 9/1998 | Bonte et al. .............. 424/195.1 |
| 5,972,366 | A |   | 10/1999 | Haynes et al. .............. 424/422 |
| 5,994,325 | A |   | 11/1999 | Roufa et al. ................... 514/59 |
| 6,020,326 | A |   | 2/2000 | Roufa et al. ................... 514/59 |
| 6,083,930 | A |   | 7/2000 | Roufa et al. ................... 514/54 |
| 6,087,549 | A |   | 7/2000 | Flick ............................. 602/41 |
| 6,093,398 | A |   | 7/2000 | Khaw et al. .............. 424/146.1 |
| 6,127,348 | A |   | 10/2000 | Roufa et al. ................... 514/59 |
| 6,156,334 | A | * | 12/2000 | Meyer-Ingold et al. ..... 424/443 |

FOREIGN PATENT DOCUMENTS

WO     WO 98/00180     1/1998

* cited by examiner

Primary Examiner—Gollamudi S. Kishore
Assistant Examiner—Isis Ghali
(74) Attorney, Agent, or Firm—Whitham, Curtis & Christofferson, P.C.

(57) ABSTRACT

The invention provides wound dressings and methods of their use, especially for the treatment of chronic, non-healing wounds. The wound dressings are composed of a support matrix, such as cotton cellulose, and an active agent associated with the support matrix. The active agent may be a protease inhibitor or a protease sequestrant, in particular an inhibitor or sequestrant of a neutrophil-derived cationic protease such as elastase.

4 Claims, 6 Drawing Sheets

PREPARATION OF PEROXIDE-OXIDIZED, SULFONATED, AND PHOSPHORYLATED COTTON

CROSS-REFERENCE TO RELATED APPLICATIONS

This application is a continuation-in-part of U.S. patent application Ser. No. 09/515,172, entitled "Wound Dressing with Protease-Lowering Activity," filed on Feb. 29, 2000, that is incorporated herein in entirety by reference.

DESCRIPTION

This invention was made in part with grants from the National Institutes of Health under grant numbers GM 20298 and NRSA GM 19122. The government may have certain rights in this invention.

BACKGROUND OF THE INVENTION

1. Field of the Invention

The invention generally relates to wound dressings and their methods of use. In particular, the invention provides wound dressings with associated active agents such as protease inhibitors and sequestrants which enhance the healing of wounds, especially chronic wounds.

2. Background of the Invention

The normal response to tissue injury is a timely and orderly reparative process that results in sustained restoration of anatomic and functional integrity. (Lazarus, et al. 1994). In contrast, in chronic ulcers, the healing process is prolonged, incomplete and proceeds in an uncoordinated manner resulting in poor anatomical and functional outcome. Clinically, wounds are categorized as acute and chronic based on the timeliness of healing.

Most chronic ulcers are associated with a small number of well-defined clinical entities particularly chronic venous stasis, diabetes mellitus, and pressure ulcers. These conditions are responsible collectively for approximately 70% of all chronic ulcers (Nwomeh et al. 1998). The incidence and prevalence of chronic ulcers vary considerably but are especially high in spinal cord injury patients as well as the elderly and nursing home population. As our society continues to age it is predicted that the incidence of chronic ulcers will continue to increase dramatically. Patients with pressure ulcers also have a significant socioeconomic impact on our society. For example, health care expenditures for treating pressure ulcers alone have been estimated to exceed $3 billion a year (Nwomeh, et al. 1998).

Normal healing involves a complex cascade of events involving interaction among many cell types, soluble factors and matrix components. Healing can be arbitrarily divided into overlapping temporal phases of coagulation, inflammation fibroplasia and finally remodeling. Most of the events are cytokine regulated. Normally, during the inflammatory phase, polymorphonuclear leukocytes(PMNs) are the first of the leukocytes to appear. They produce various proteases such as MMP-8 (collagenase) and elastase, which help to remove damaged matrix and aid in healing. In both the open acute and chronic wound, various cytokines are important in contraction and spontaneous closure of the wound as well as angiogenesis. Under normal circumstances, closure of the open wound is aided further by epithelization as these surface cells seal the final closure.

Chronic wounds are very different. For example, pressure ulcers are characterized by deep tissue necrosis with loss of muscle and fat that is disproportionately greater then the loss of overlying skin (Falanga, et al. 1998). These defects are common among the immobilized and debilitated. There are approximately 225,000 spinal cord injury patients in the United States and approximately 9,000 new cases per year. Approximately 60% of these patients develop pressure ulcers and the annual cost is greater then $25,000 per patient for medically related care. (Allman, 1998) If the elderly nursing home population with pressure ulcers in added to the spinal cord injury population then the figure for the care of all pressure ulcers is enormous.

To date, the majority of the effort to improve rates of healing of chronic wounds have focused on the use of exogenous peptide growth factors and cell based products such as cytokines. For the most part, these attempts have met with little notable success. Another alternative approach has been the use of "skin substitutes" such as Apligraf (matrix+ cells) and Dermagraft (matrix+cells). While this second approach has shown some promise, its expense presently greatly limits its use to the richer developed countries. Various modifications of the wound dressings have also been suggested as a means to augment would healing.

Further examples include:

U.S. Pat. No. 5,098,417 to Yamazaki et al. teaches the ionic bonding of physiologically active agents to cellulosic wound dressings.

U.S. Pat. No. 4,453,939 to Zimmerman et al. teaches the inclusion of aprotonin in composition for "sealing and healing" of wounds.

U.S. Pat. No. 5,807,555 to Bonte et al. teaches the inclusion of inhibition for alpha-1-protease, collagenase, and elastase in pharmaceutical compositions for promotion of collagen synthesis.

U.S. Pat. No. 5,696,101 to. Wu et al., teaches use of oxidized cellulose (e.g. Oxycel) as a bactericide and hemostat in treatment of wounds.

World Patent WO 98/00180 to Watt et al. teaches complexation of oxidized cellulose with structural proteins (e.g. collagen) for chronic wound healing; and references the utility of oligosaccharide fragments produced by the breakdown of oxidized cellulose in vivo in the promotion of wound healing.

Neutrophils are a predominant infiltrating inflammatory cell type present in the acute inflammatory response. Neutrophils function primarily to destroy invading pathogens and to debride devitalized tissue at the site of injury. The normal adult produces approximately $10^{11}$ neutrophils per day. To function effectively in host defense, they must migrate to the site of inflammation and release selectively a large repertoire of lytic enzymes, antimicrobial peptides, and potent oxidants from cytoplasmic granules. Under other conditions, the neutrophil has been implicated in causing disease by damaging normal host tissue. Such inflammatory tissue injury are important in the pathogenesis of a variety of clinical disorders including arthritis, ischemia-reperfusion tissue injury and systemic inflammatory response syndrome (SIRS) and the acute respiratory distress syndrome (ARDS). (Weiss, 1989) There is strong evidence that neutrophils also may have a significant role in the pathophysiology of pressure ulcers.

Neutrophils are a prevalent cell type in pressure ulcers. (Diegelmann, et al. 1999; Paloahti, et al. 1993; Rogers et al. 1995) In addition, there is direct evidence correlating neutrophil products with chronic pressure ulcers. (Yager, et al. 1996; Yager, et al. 1997). This includes neutrophil elastase, gelatinase (MMP-9) as well as collagenase (MMP-8). (Wysocki, 1996; Wysocki et al, 1993; Yager et al. 1997;

Yager et al. 1996). Therefore, these observations and the evidence that neutrophils have been implicated in tissue destruction in other inflammatory processes give strong credence to the hypothesis that neutrophil products are involved in the pathogenesis of pressure sores and subsequent failure to heal. Neutrophil-derived MMP-8 has been shown to be the predominant collagenase in both acute and chronic wounds. (Nwomeh, et al. 1999).

Neutrophils contain large amounts of elastase (1 pg/cell). This serine protease has a broad substrate spectrum. As with neutrophil-derived MM-8, elastase levels have also been found to be significantly elevated in fluid derived from pressure ulcers. (Yager et al. 1997) The presence of high levels of active elastase with a wound site may have important implications for wound healing therapies utilizing peptide growth factors. Elastase present in chronic wounds can degrade peptide growth factors such as PDGF and TGF-b. (Yager et al. 1997). Moreover, cell surface receptors for peptide growth factors may themselves be functionally inactivated by the actions of elastase. Elastase may also contribute to the overall proteolytic environment of chronic wounds. It is known to proteolytically inactivate the specific inhibitor, Tissue Inhibitor of Metalloproteinases (TIMP). In addition, elastase itself may participate in proteolytically activating collagenase and gelatinase zymogens. Obviously, an unregulated proteolytic environment can be a significant aspect of the pathophysiology of chronic wounds.

It would be highly beneficial to have available additional methods for enhancing wound healing. In particular, methods directed to bringing the proteolytic environment of wounds under control in order to promote wound repair would be desirable. Such methods would be useful in the treatment of wounds in general, and chronic wounds in particular. Further, it would be highly beneficial if such methods were inexpensive and thus widely accessible.

SUMMARY OF THE INVENTION

It is an object of this invention to provide novel wound dressings for the treatment of wounds, especially for the treatment of chronic, non-healing wounds. The wound dressings of the instant invention are comprised of a support matrix and an active agent associated with the support matrix. In preferred embodiments of the invention, the support matrix is cellulose or carboxymethylated cellulose.

The active agents may be protease inhibitors. Protease inhibitors especially suited to the practice of the instant invention include those which inhibit neutrophil-derived proteases, an overabundance of which are found in chronic wounds. In particular, these are cationic proteases, such as elastase. Examples of such inhibitors include peptide inhibitors such as di- or tri-peptide sequence such as Val-Pro, Pro-Val, Ala-Pro-Val or Val-Pro-Ala; or tetrapeptide sequences containing Ala-Pro-Val or Val-Pro. These inhibitors may be associated with the support matrix via covalent, non-covalent or ionic linkages. Further, the inhibitors may be dissociable from the matrix. Upon exposure to the wound fluid, the inhibitors may be released from the matrix and migrate into the wound microenvironment.

The active agents may also be sequestrants. Substances suitable as sequestrants may also be protease inhibitors (as listed above). Alternatively, sequestrants may be of a more general nature, for example, sulfonyl, phosphate, or aldehyde groups associated with the support matrix. The sequestrants bind proteases found in the wound fluid and remove them from the wound microenvironment.

The invention also provides methods of use for the wound dressings, including a method for sequestering elastase at a wound site. This method comprises the step of contacting the wound site with a wound dressing selected form the group consisting of carboxymethylcellulose, dialdehyde gauze, sulfonated gauze, and phosphorylated gauze.

The dressings may be applied to wounds in order to enhance would healing, especially the healing of chronic wounds.

DETAILED DESCRIPTION OF THE PREFERRED EMBODIMENTS OF THE INVENTION

Figure 1A:
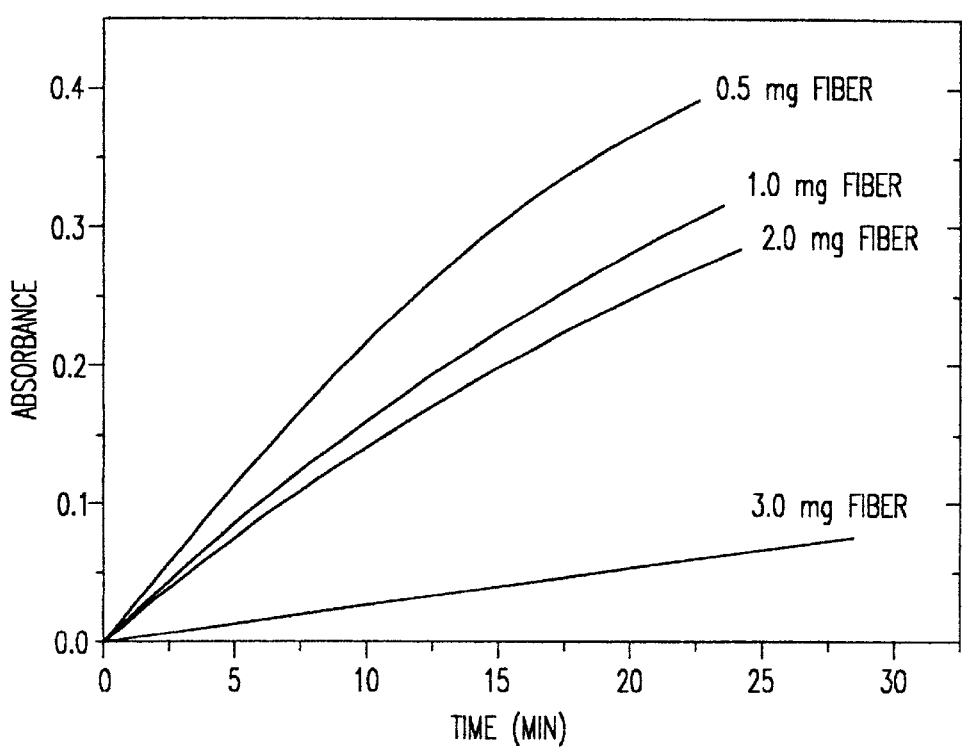
FIGS. 1A and 1B. Reaction progress curves for the inhibition of HLE by fiber-inhibitor (1A) and known HLE inhibitor MEOSuc-Val-Pro-Val-chloromethylketone (1B).

The present invention is based upon the previously unrecognized discovery that active agents such as inhibitors and sequestrants of proteases may be used as healing accelerants of wounds, and of chronic wounds in particular. These inhibitors and sequestrants may be physically applied on wound dressings, or in the alternative may be ionically or covalently conjugated to a wound dressing material for purposes of sustained release of active agent or sequestration of endogenous constituents from the wound environment. In a preferred embodiment of the present invention, the active agents inhibit or bind cationic, neutrophil-derived proteases such as neutrophil elastase.

The term active agent is meant to include (but not be limited to) protease inhibitors and protease sequestrants. Those of skill in the art will recognize that the two categories are not, however, mutually exclusive. They may overlap in that a protease inhibitor may also function as a sequestrant, and a sequestrant may or may not also inhibit the protease. Further, the term "active agent" is meant to encompass 1) substances that are associated with the wound dressing as a result of having been added to the wound dressing (either chemically attached or otherwise physically compositioned onto the dressing), and 2) functional groups that are inherent within the wound dressing material itself and derivatives and chemical modifications of such functional groups. An example of the latter is the hydroxyl groups of cellulose.

The term protease inhibitor is meant to include those materials which effect a diminution in protease activity. Such inhibitors may include, for example, inhibitors of the active site of the protease, allosteric inhibitors, reversible and irreversible inhibitors, substrate analogs of various types, peptides and peptidemimetics, antibiotics, and the like. In a preferred embodiment of the instant invention, the protease inhibitor inhibits a neutrophil-derived protease. In yet another preferred embodiment, the neutrophil-derived protease is neutrophil elastase.

Examples of protease inhibitors which may be utilized in the practice of the present invention include but are not limited to: an alkyl amino acid such as Ala, Leu, Ile, Val, and Nle; a di- or tri-peptide sequence such as Val-Pro, Pro-Val, Ala-Pro-Val or Val-Pro-Ala; tetrapeptide sequences containing Ala-Pro-Val or Val-Pro- and possessing as a terminal residue amino acids such as Ala, Lys, Arg, Trp, Phe, Gln, His, and Tyr. Such inhibitors may be linked through the amino- or carboxy-terminus to the wound dressing material via, for example, a salt bridge. Alternatively, the inhibitors may be embedded in or otherwise associated with the wound dressing material. When the inhibitor is an amino acid or peptide, it may also be derivatized at its amino- or COOH-terminus as, for example, an acid, carboxamide, alcohol, ester, ketone, aldehyde, ketomethylester, α-ketoesters, methyl chloroformate, pentafluoroethylketone, trifluoromethylketones, boronic acids or oleic acid. The inhibitor may also be alpha-antitrypsin or any protein serine protease inhibitor.

In the case of protease inhibitors, they may either be immobilized on the matrix, or they may be releasable into the wound fluid. For example, covalently associated inhibitors may be released via hydrolysis. Or inhibitors that are compositioned onto the matrix may be released simply by hydration and dissolution into the wound fluid. The released inhibitors are then free to migrate into the wound fluid in order to exert their beneficial effect (inhibiting deleterious proteases) throughout the wound microenvironment.

The term sequestrant is meant to include active agents capable of binding and retaining a protease in a manner which removes the protease from the wound bed. The concentration of the protease in the wound environment is thus decreased. The sequestrant may be specific for the protease, e.g. designed to bind to the protease active site (either reversibly or irreversibly), or designed to bind to some other distinguishing feature of the protease. For example, the sequestrant may be an antibody directed to an epitope of a protease or a class of proteases. Alternatively, binding may be of a more general nature. For example, binding may be directed to a general class of proteases such as the cationic proteases. In this case, the active agent may be an anionic group such as phosphate, sulfate, carboxylate, and the like. The anionic group may be attached directly to the wound dressing material (e.g. to the hydroxyl functions of cellulose cotton) or may be attached to the wound dressing material indirectly by means of a linking group such as an alkyl chain. Further, the anionic group may be part of another substituent that is associated with the wound dressing material, e.g. the anion may be the carboxyl function of an amino acid or peptide, or a phosphate group that is attached to an amino acid or peptide. Any rationally designed inhibitor or sequestrant that may be directly linked to the support matrix and which possesses affinity for the protease may be utilized in the practice of the present invention.

Specific pharmacological effects of proteases inhibitors and sequences associated with wound dressings include inhibition of the breakdown of growth factors that stimulate migration of cells to the ulcer site of the wound, leading to the growth of new tissue that heals the open wound. This technology is broadly applicable to all forms of chronic wounds including diabetic ulcers and decubitus bedsores. Both peripheral and central administration of the compounds formulated on wound dressings accelerate wound healing of chronic wounds. The compounds of this invention may be applied to wound dressings as agents that may be released into the wound and thereby inhibit proteases such as human elastase and thus prevent growth factor and tissue degradation. Alternatively, the inhibitors of this invention are covalently bound to the wound dressing. As a component of such a matrix, they are able to sequester destructive proteases from the microenvironment of the wound, thus preventing the degradation of growth factors and fibronectin that would otherwise occur.

The therapeutic administration of the modified wound dressings containing inhibitors include a pharmacologically effective dose of the inhibitor or sequestrant when used in the treatment of a patient in need thereof. The dose of inhibitor or sequestrant required on the wound dressing to promote accelerated healing in the patient ranges from about 0.2 mg/gram fiber to about 200 mg/gram fiber per day, with this in turn being dependent upon specific factors including patient health, wound type, and specific protease inhibitor/sequestrant utilized. The amount of active agent required can be readily determined by those skilled in the art.

The term "patient" used herein is taken to mean mammals such as sheep, horses, cattle, pigs, dogs, cats, rats, mice and primates, including humans.

The term "wound dressing" used herein is taken to include any pharmaceutically acceptable wound covering or support matrix such as:

a) films, including those of a semipermeable or a semi-occlusive nature such as polyurethane copolymers, acrylamides, acrylates, paraffin, polysaccharides, cellophane and lanolin.

b) hydrocolloids including carboxymethylcellulose protein constituents of gelatin, pectin, and complex polysaccharides including Acacia gum, guar gum and karaya. These materials may be utilized in the form of a flexible foam or, in the alternative, formulated in polyurethane or, in a further alternative, formulated as an adhesive mass such as polyisobutylene.

c) hydrogels such as agar, starch or propylene glycol; which typically contain about 80% to about 90% water and are conventionally formulated as sheets, powders, pastes and gels in conjunction with cross-linked polymers such as polyethylene oxide, polyvinyl pyrollidone, acrylamide, propylene glycol.

d) foams such as polysaccharide which consist of a hydrophilic open-celled contact surface and hydrophobic closed-cell polyurethane.

e) impregnates including pine mesh gauze, paraffin and lanolin-coated gauze, polyethylene glycol-coated gauze, knitted viscose, rayon, and polyester.

f) cellulose-like polysaccharide such as alginates, including calcium alginate, which may be formulated as non-woven composites of fibers or spun into woven composites.

Preferred wound dressings are polysaccharide containing support matrices capable of ionically or covalently bonding the active agents thereto, or having the active agent compositioned with or upon, and is envisioned to include chitosans, alginates and cotton or carboxymethylated cotton in the form of gauze, films, hydrocolloide, hydrogels, hydroactives, foams, impregnates, absorptive powders and pastes, as known in the art and described in USP 24:NP 19; The United States Pharmacopeia: The National Formulary, USP 24:NF 19, United States Pharmacopeial Convention, INC., Rockville, Md., Jan. 1, 2000, incorporated by reference herein.

Especially preferred wound dressings include cotton cellulose formed as woven or non-woven gauze. This type of wound dressing has the advantage of being readily available and relatively inexpensive. In this case, the protease sequestrant or inhibitor may be linked to the cellulose polysaccharide chain through a chemical substituent such as amino, carboxylate, citrate, phosphate, sulfonate, chloride, bromide, mono-carboxylic acid, di-carboxylic acid, tri-carboxylic acid; or, any pharmaceutically acceptable salt thereof. Exemplary salts are seen to include those of acids such as acetic, glycolic, lactic, pyruvic, malonic, succinic, glutaric, fumaric, malic, tartaric, ascorbic, maleic, hydroxymaleic, benzoic, hydroxybenzoic, phenylacetic, cinnamic, salicylic, and 2-phenoxyhenzoic; and sulfonic acids such as methane sulfonic acid and hydroxyethane sulfonic acid. Salts of the carboxy terminal amino acid moiety may include the non-toxic carboxylic acid salts formed with any suitable inorganic or organic bases. illustratively, these salts include those of alkali metals, as for example, sodium and potassium; alkaline earth metals, such as calcium and magnesium; light metals of Group IIA elements including aluminum, and organic primary, secondary, and tertiary amines, as for example, trialkylamines, including triethylamine, procaine, dibenzylamine, 1-ethenamine, N,N'-dibenzylethylenediamine, dihydroabietylamine, N-alkylpiperidine and any other suitable amine.

The active agents may be applied as a reactively bound constituent of a wound dressing or may be compositioned for application to a treatment site via moistened fibers in the dressing. Dressing systems may be either single or multi-phase; with the one-phase system consisting of the wound dressing with the active agent. An exemplary multi-phase system would employ the wound dressing and a suspension of a physiologically acceptable diluent. Exemplary pharmaceutical carriers which may function as the diluent can be a sterile physiologically acceptable liquids such as water and oils and may optionally further contain surfactants and other pharmaceutically acceptable adjuvants.

An exemplary but non-exhaustive list of oils which can be employed in these preparations are those of petroleum, animal, vegetable, or synthetic origin, for example, peanut oil, soybean oil, and mineral oil. in general water, saline, and glycols, such as polyethylene glycols are preferred liquid carriers.

The wound dressings of the instant invention may be used alone or as an adjunct to other therapeutic measures. For example, the wound dressings may be used together with the administration of exogenous growth factors. Obviously, conditions that increase the stability of an exogenous peptide growth factor or its receptor will likely promote its efficacy. The wound dressings of the present invention may also be used in conjunction with skin grafts, in which case a proteolytic environment that is under control will less likely cause the "rejection" or melting of a skin substitute graft.

Further, the wound dressings of the present invention may be comprised of a single active agent, or of a plurality of active agents on the same dressing. For example, a sequestrant and an inhibitor may both be associated with the wound dressing. Or a releasable inhibitor and a sequestrant may both be associated with the wound dressing. The wound dressings may also include other therapeutically beneficial substances such as antibiotics, vitamins, and the like.

The dressings and methods of the present invention may be utilized to treat any type of appropriate wound. In a preferred embodiment, the wound that is treated is a chronic, non-healing wound.

The invention is illustrated by the following Examples which are intended to be illustrative but should in no way be construed as limiting.

EXAMPLES

Abbreviations:
CMC: carboxymethyl cellulose
DIC: diisopropyl carbodiimide
DIPEA: diisopropylethylamine
DMAP: dimethylaminopyridine
DMF: dimethyl formamide
DMSO: dimethyl sulfoxide
DS: degree of substitution
EDCI: N'-ethyl-N'-(3-dimethylaminopropyl)carbodiimide hydrochloride
FAB MS: fast atom bombardment mass spectrometry
Fmoc: 4-fluoronylmethyloxycarbonyl
HLE: human neutrophil elastase
HOBT: hydroxybenzotriazole
NMI: N-methylimidazole
NMM: N-methylmorpholine
TFA: trifluoroacetic acid Example 1
Assessment of Elastase Sequences as Sequestrants
Methods
General Synthesis and Formulation of Conjugates of Cotton Cellulose and Inhibitor Sequences.

Desized, scoured, bleached and mercerized cotton gauze was used for the synthesis. The cotton twill fabric was cut as circular discs (8.5 cm. in diameter) for the synthesis.

Carboxymethylated cotton cellulose was prepared by refluxing 100% cotton twill (290 grams) for one hour with 25% monochloroacetic acid in a sodium hydroxide solution of methanol:isopropanol (13:87, v:v) and 0.5% TX-100. The degree of substitution of carboxymethylation or carboxyl content was determined by measuring the carboxyl content of the cotton with an acid base titration. The carboxyl content was calculated from the following equation:

$$DS=[(162)(\%COOH)]4500-(R)(\%COOH)$$

where R is the molecular weight of the ether substituent minus one i.e., 58 for carboxymethylcellulose.

Esterification of cotton cellulose was accomplished through base-catalyzed carbodiimide/HOBT acetylation.

Cotton samples used in the synthesis were pre-treated with 20 ml 25% TFA/DCM (10 min), washed with 5×20 ml DCM, 2×20 ml, 10% DIPEA, 5×20 ml (5 min), and 2×20 ml DCM. The cotton discs were vacuum dried on a Buchner funnel, and esterified in a beaker placed in an ultrasonic bath. Fmoc-glycine esterification was accomplished by reacting the cotton discs in a 20 ml DMF solution with 0.3 M Fmoc-Glycine/DIC/HOBT and 0.03 DMAP. The cotton discs were washed with DMF and water and glycine estimated from amino acid analysis to be 200 micromoles/gram of cotton. Cotton samples of this type prepared with glycine linkers may then be used to assemble peptide sequences or may be used to form the counterion of a peptide or amino acid carboxy salt. Thus the amino salts of glycine cotton cellulose conjugates may be formed with elastase peptide inhibitors illustrative of the claims.

Val-Pro-Val-Gly Peptide Synthesis on Cotton Cellulose

The Val-Pro-Val recognition sequence was synthesized with glycine as a COOH-terminal linker on 8.5 cm discs of cotton twill. The synthetic protocol for the synthesis of Val-Pro-Val-Gly on cotton consisted of the following steps as described by Eichler et al, 1991. Acetylation of Fmoc-Gly-bound cellulose cotton was accomplished with acetic anhydride/NMI/DMF 1:2:3 (v/v/v) for 60 min. The cotton discs were washed with DMF (3×10 mL) and DCM (2×10 mL).

Deprotection of Fmoc was accomplished in 20% piperidine/DMF, 15 min; wash (3× DMF, 2× DCM); coupling (0.3M Fmoc-amino acid/HOBT/DIC in DMF, 90 min); wash (3× DMF; 2× DCM). Ten microliters of a bromophenol blue/DMF solution was added. during the coupling step. Two hundred milligram samples were subjected to amino acid analysis. The resulting ratio of amino acids from the analysis was 1:2 (Pro:Val) and the resulting yield was 1.1 micromoles/gram cotton.

Synthesis of Val-Pro-Val-O-Methylester

A solution of carbobenzoxy-Val-Pro-OH (1 g, 2.8 mmol) in 30 ml of dry tetrahydrofuran was cooled to −5° C. and N-methylmorpholine (0.29 g, 2.8 mmol) and isobutyl chloroformate (0.391 g, 2.8 mmol) were added and stirred for 1 h. A solution of Val-OMe (0.49 g, 2.8 mmol) in dioxane/water (7:3) was adjusted to pH 7 with diisopropylethylamine. The solutions were combined and the mixture stirred for 3 h, water added and the tetrahydrofuran evaporated. The resulting oil was extracted with ethyl acetate and subjected to a work-up of 1 N HCl, saturated NaCl, and drying over sodium sulfate yielding a clear oil. The product was confirmed by FAB MS ([M+1]=463) and the N-protecting group was removed by catalytic hydrogenolysis using ammonium formate. (Anwer, M. K., & Spatola, A. F. (1980) Synthesis 11, 929–932). The product Val-Pro-Val-OMe may be used in the formation of carboxymethylcellulose-Val-Pro-Val-OMe conjugate.

Synthesis of Carboxymethylcellulose-Val-Pro-Val-OMe Conjugate

Two carboxymethylated cotton discs (circular 8.5 cm discs weighing 2.6 g each with a degree of substitiution of ~25%) were reacted with 0.15M Val-Pro-Val-OMe/HOBT/DIC in 10 ml DMF mixed in a beaker and placed in an ultrasonic bath. The reaction was monitored with bromophenol blue (20 uL, 0.01 M bromophenol), and was allowed to proceed overnight. Conversion of blue to yellow signals completion of the reaction. Three hundred milligram samples of the cotton cellulose conjugates were subject to amino acid analysis. The resulting ratio of amino acid from the analysis was 1:2 (Pro:Val) and the resulting yield was 8.5 micromoles/gram cotton.

Preparation of Carboxymethylcellulose-Ala-Ala-Pro-Valine-chloromethylketone and its Cotton Conjugate A stirred suspension of N-tosyl-L-valine acid chloride (0.95 g, 3 mmoles) in anhydrous ether (30 mL) was treated in an ice bath with ethereal diazomethane (6 mmoles) in anhydrous ether. The reaction mixture was left overnight, then treated with dry hydrogen chloride for 2 h. The chloroketone is obtained on removal of the solvent. A solution of carbobenzoxy-Ala-Ala-Pro-OH (2.8 mmol) in 30 ml of dry tetrahydrofuran was cooled to −5° C. and N-methylmorpholine (0.29 g, 2.8 mmol) and isobutyl chloroformate (0.391 g, 2.8 mmol) were added and stirred for 1 h. A solution of N-tosyl-L-valine chloromethylketone (2.8 mmol) in dioxane/water (7:3) was adjusted to pH 7 with diisopropylethylamine. The solutions were combined and the mixture stirred for 3 h, water added and the tetrahydrofuran evaporated. The resulting oil was extracted with ethyl acetate and subjected to a work-up of IN HCl, saturated NaCl, and drying over sodium sulfate yielding a clear oil. The N-protecting group was removed by catalytic hydrogenolysis using ammonium formate. The resulting product was filtered and lyophilized to give the peptide Ala-Ala-Pro-Val-chloromethylketone. Two carboxymethylated cotton discs (circular 8.5 cm discs weighing 2.6 g each with a degree of substitution, 25%) were reacted with Ala-Ala-Pro-Val-pentafluoroethylketone/HOBT/DIC in 10 ml DMF mixed in a beaker and placed in an ultrasonic bath. The reaction was monitored with bromophenol blue (20 uL, 0.01 M bromophenol), and was allowed to proceed overnight. Conversion of blue to yellow signals completion of the reaction. Three hundred milligram samples of the cotton cellulose conjugates were subject to amino acid analysis The resulting ratio of amino acid from the analysis was 2:1:1 (Ala:Pro:Val) and the resulting yield was 0.484 micromoles/gram cotton.

Stepwise Preparation of Carboxymethycellulose-Ala-Ala-Pro-Val-pentafluoroethylketone and its Cotton Conjugate Step 1. Preparation of Boc-Valyl-N-methyl-o-methylcarboxamide To a solution of N-(tert-butoxycarbonyl)-L-valine in ethylene chloride was added dimethylaminanopyridine, N,O,-dimethylhydroxylamine hydrochloride, NMM and EDCI and the solution was stirred at room temperature for 20 h. The solution was washed with 10% HCl, saturated NaHCO$_3$ and brine, and the solvent was removed in vacuo to give a colorless oil.

Step 2. Preparation of Boc-Valyl-pentafluoroethylketone.

To a −78° C. solution of Boc-Valyl-N-methylmethylcarboxamide was added condensed pentafluoroethyliodide. To the mixture was added methyllithium-lithium bromide complex while maintaining an internal reaction temperature below −65° C. The reaction mixture is stirred at −65° C. to −78° C. for 1.5 h. The mixture was poured into water and the aqueous phase was acidified with potassium hydrogen sulfate. The aqueous phase was extracted with additional Et$_2$O (500 ml), and the combined organic extracts were washed with saturated NaHCO$_3$ and dried over Na$_2$SO$_4$.

Step 3. Preparation of Boc-Ala-Ala-Pro-Val-pentafluoroethylketone.

A solution of Boc-Valyl-pentafluoroethylketone in trifluoroacetic acid; methylene chloride (1:1, v:v) was prepared and allowed to react for 30 min. The solvent was removed in vacuo and the resulting deprotected peptide reacted with Boc-Ala-Ala-Pro-OH through diisopropycarbodiimide/HOBT coupling.

Further preparation of carboxymethyl cellulose-O-Ala-Ala-Pro-Val-pentafluoroethylketone is as follows:

Two carboxymethylated cotton discs (circular 8.5 cm discs weighing 2.6 g each with a degree of substitution, 25%) were reacted with 0.15M Ala-Ala-Pro-Val-pentafluoroethylketone/HOBT/DIC in 10 ml DMF mixed in a beaker and placed in an ultrasonic bath. The reaction was monitored with bromophenol blue (20 uL, 0.01 M bromophenol), and was allowed to proceed overnight. Conversion of blue to yellow signals completion of the reaction. The cotton is then washed with 20 mL of DMF three times followed by three washes with methylene chloride. The resulting peptido-cellulose conjugates on cotton were subjected to amino analysis and found to contain 30 micromoles of peptide per gram of cotton.

Preparation of Propyl-3-keto-(2.3, 6)-O-Cellulose Ether.

Four grams of cotton cellulose was suspended in a 300 ml solution of dioxane and water (2:1) whereupon Dabco (1,4-diazabicyclo[2.2.2.]octane) was added to pH 8, and 0.0246 moles of vinylpropylketone was added. The suspension is allowed to stir overnight. Alternatively, the treated gauze soaked with the solution of base and vinylpropyketone may be cured at 100° C. for one hour and the product rinsed with cold water for 30 minutes followed by drying at 85° C.

Preparation of Levulinate-(2,3,6)-O-Cellulose Ester

Esterification of cotton cellulose gauze with levulinic acid was accomplished by reacting the cotton discs in a 20 ml DMF solution with 0.3 M levulinic acid/DIC/1-HOBT and 0.03 M DMAP. The esterification may also be performed under aqueous conditions with a water soluble carbodiimide at the same molar concentrations via convention pad and cure techniques employing citric acid and sodium hypophosphite crosslinking of the levulinic acid.

Preparation of Glucose-6-citrate-(2,3,6,)-O-Cellulose Ester.

Two gram samples of cotton gauze were padded with two dips and two nips in a four percent solution of sodium hypophosphite, a 0.62 M citric acid and a 0.12 M glucose solution on a laboratory mangle. The padded gauze were dried and cured in ovens with mechanical circulated air. Curing temperatures were set at 180° C., and drying at 85° C. The resulting add-on weight of product was found to be 11% or an 11% increase in weight based on the difference before and after the wet finishing modification.

Ten milligrams of Ala-Pro-Val-Chloromethylketone acetate salt was dissolved in a 0.05 M saline solution and applied to 2 grams of carboxymethylated cotton gauze to saturation. The gauze was then lyophlized to dryness and a cotton cellulose sample taken for amino acid analysis revealing 10 micromoles of peptide per gram of cotton gauze.

Results

Chromatography was performed to measure the affinity of the cotton cellulose-bound recognition sequences for elastase, and the ability of the cotton fiber conjugates to sequester the elastase from an aqueous environment. Since the synthesis was performed on mercerized cotton, mercerized cotton was compared with unmercerized cotton as a chromatographic stationary phase for elastase elution. Less elastase was retained (4%) in the untreated mercerized cotton column compared to untreated unmercerized (12%). This might be expected since the crystallinity of the cotton fiber undergoes a change upon mercerization. Table 1 outlines the comparative levels of elastase retained, expressed as percent of retained elastase on the cotton columns. The comparative levels of elastase retained on the columns under physiological saline conditions suggests the ability to sequester elastase from wound fluid. Two series of elastase retention measurements were made based on the first injection of elastase to the freshly prepared column and subsequent percent elastase retained. The percent of retained elastase following the first injection was higher for all samples when compared with the repetitive injections.

Conjugate I gave the highest retention of elastase. Fifty eight percent of elastase was retained on conjugate I as compared with the CMC control of thirty percent on the first pass of elastase solution over the column. Conjugate I is a COOH-terminal methyl ester of Val-Pro-Val attached to carboxymethylated cellulose at the amino-terminal valine. This results in the COOH-terminus being more accessible for enzyme binding. The cotton cellulose conjugate Val-Pro-Val-Gly sequence attached through the COOH-terminal glycine to cotton cellulose retained less elastase (26%) from the first injection. The percent elastase retained with repetitive injections followed a similar trend to the first-injected samples among the analogs tested. Conjugate I demonstrated the highest average retention of elastase (37%).

TABLE 1

Elastase Retention on Peptido-Cellulose Columns[1]

| Cotton | Description of Cotton Conjugates | % Elastase Retained ± SD[2] |
|---|---|---|
| I | Carboxymethylated Cellulose -Val-Pro-Val-OMe | 37 ± 0.71 |
| II | Val-Pro-Val-Gly-Cellulose | 26 ± 0.71 |
| III | Carboxymethylated Cellulose Cotton | 32 ± 2.12 |
| IV | Unmercerized Cotton Twill | 12 ± 1.63 |
| V | Cellulase-treated Cotton | 15 ± 0.35 |
| VI | Val-Pro-Pro-Gly-Cotton (Cellulase treated) | 12 ± 2.47 |
| VII | Mercerized Cotton Twill | 4 ± 1.41 |

[1]Elastase was injected onto the cotton conjugate columns as described.
[2]Percent elastase retained represents the average of triplicate injections on the same columns.

These results demonstrate that peptide sequences that are covalently attached to a cellulose support can effect the sequestration of proteases for which they are inhibitory.

Example 2

Inhibition of Elastase by a Synthetic Cotton-Bound Protease Inhibitor

Materials and Methods

The peptide substrate and inhibitor, including MeO-Suc-Ala-Ala-Pro-Val-p-nitroanalide and MeO-Suc-Ala-Ala-Pro-Val chloromethyketone, respectively were obtained from Sigma (St. Louis, Mo.) and their purity confirmed by Reversed Phase High Performance Liquid Chromatography (RPHPLC) prior to experimental use. Leukocyte elastase (Sigma, St. Louis, Mo.) obtained from human leukocytes (HLE) was solubilized from 1 unit vials (one unit of HLE will release one nanomole of p-nitrophenol per second from N-t-Boc-Alanine p-nitrophenylester at pH 6.5) and 0.2 unit aliquots employed per reaction. Cotton fibers were taken from woven cotton twill, which was desized, scoured, bleached and washed. The woven cotton was pretreated with the cellulase enzyme, Cellusoft, and a 10% solution of trifluoroacetic acid in methylene chloride followed by three washes with methylene chloride. The cotton fabric was pretreated with cellulase to remove the non-cellulose constituents of the primary cell wall of he cellulose cotton and improve binding of the peptide CMK.

Preparation of Fiber-Inhibitor Formulation

As a model to demonstrate the optimal conditions for formulations, enzyme inhibition, and in vitro release, a low molecular weight COOH-terminally modified tetrapeptide ketone was impregnated into cotton fibers. Acetonitrile solutions (0.5 ml) of the MeO-Suc-Ala-Ala-Pro-Val chloromethyketone (1.2 mg/ml) were applied to separate 300 mg samples of cotton twill fabric. The use of acetonitrile in the application provides for rapid diffusion of the inhibitor solution into the fabric. The inhibitor is thought to bond non-covalently to the polysaccharide chain of the cellulose fibers through hydrogen bonding. The fabric was made slightly acidic through pre-treatment with trifluoroacetic acid solution to promote acid catalyzed formation of a hemiketal between the peptide ketone and accessible hydroxyls of the glucan rings in cellulose. This would form a more durable affinity of the inhibitor for the cotton cellulose, which is hydrolyzed under aqueous conditions. Hemiketals are released to their corresponding ketones when hydrated. Samples were allowed to air dry and pulverized in a Wiley Mill of 80 mesh screen (150 micron size fibers). The pulverized samples were lyophilized to remove trace amounts of acetonitrile.

Enzyme Assays

Enzyme assays of HLE were conducted in pH 7.6 buffer composed of 0.1M sodium phosphate, 0.5 M NaCl, and 3.3% DMSO and subjected to spectrophotometric measurement of the release of p-nitoraniline at 410 nm from the enzymatic hydrolysis of MeO-Suc-Ala-Ala-Pro-Val-pNA. In a typical experiment 250 µl of enzyme solution (0.52 units, or 2.08 units.ml) of elastase was combined in a total volume of 1.5 ml buffer with 60 µM substrate. In a typical experiment fiber-inhibitor formulations were assessed for elastase inhibition by mixing milligram quantities of the pulverized cotton samples with enzyme solutions in 5 ml Reacti-Vials (Pierce Chemical Company). The cotton fiber suspension was filtered on 0.45 micron filters attached to a 5 ml syringe. The filtrate was mixed with substrate and the enzyme hydrolysis of substrate was measured spectrophotometrically.

Reaction progress curves were recorded on a Shimadzu UV-265 equipped with a recorder, and time points were obtained by applying the program Un-Scan It™ (Silk Scientific, Ogden Utah) to the recorded curves. A digitized scan produced between 280 and 450 poirs of absorbance-time data points. velocities were determined as described (Williams and Morrison) at 10–40 points along the progress curve.

Amino acid analysis was completed on an Applied Biosystems amino acid analyzer. This consisted of the Model 420A Derivatizer/Hydrolyzer where peptide samples were hydrolyzed in 6N HCl, converted to the PTC-derivatives, and chromatographically analyzed on the Model 130A, and the Model 920! Data Module.

High performance liquid chromatography studies were completed with a Beckman Systems Gold 508 autosampler, programmable solvent module 126, and diode array detector module 168 (214 nm). Data were acquired and analyzed by computer automated Gold™ Noveau software. Chromatographic analysis and separation of the elastase inhibitor was performed on a Vydac 5 micron C18 peptide reverse phase column (4.6×150 mm) with a linear gradient mobile phase of 15 to 40% acetonitrile/aqueous 0.1%TFA and a flow rate of 1 ml/min.

Patients and Wound Fluids

Fluids were harvested from seven-grade III sacral, ischial, or trochanteric pressure ulcers of five patients with spinal cord injuries. Three patients had two distinct wounds which were sampled and which were considered separate data points. Patients ranged in age from 50–65 years and had no significant comorbidities. All wounds were present for a minimum of 2 months. There was no evidence of gross infection in any of the wounds used in the study. Wound care in all but one ulcer consisted of normal saline-soaked wet to dry dressings. A small margin of one wound was receiving topical collagenase (Santyl) for enzymatic debridement. This wound was irrigated copiously with normal saline prior to collection of ulcer fluid. An occlusive dressing (Tegaderm: 3M, St Paul, Minn.) was placed over the ulcers for 2–4 hours, and fluid was collected by aspiration with a sterile tuberculin syringe. Fluids were clarified by centrifugation at 14,000 g for 15 min at 4 C. The protein concentration was determined with the Bio-Rad Protein assay (Richmond, Calif.) with bovine serum albumin as a quantitative standard.

Determination of Elastase Activity in Wound Fluid.

Elastase activity was determined by methods described previously. (Nakajima et al.) One hundred microgram amounts of protein were incubated in 1.0 ml of Hepes-NaOH buffer 100 mmole/L, pH 7.5, NaCl 500 mmole/L, 10% DMSO, containing 0 to 5 mg of cotton-bound fiber inhibitor. The heterogeneous reaction was incubated at room temperature while shaking vigorously. The inhibitor-protein mixture was then filtered through a 0.22 micron filter into a cuvette. The reaction substrate was added to each of the filtered samples to a final concentration of 100 µmol/L. Substrate hydrolysis was assessed by measuring $A_{410}$ at 5 min, 15 min, and 60 min after substrate addition. Purified neutrophil elastase was used to generate a standard curve.

Results

Elastase Inhibition Kinetics

Figure 1B:
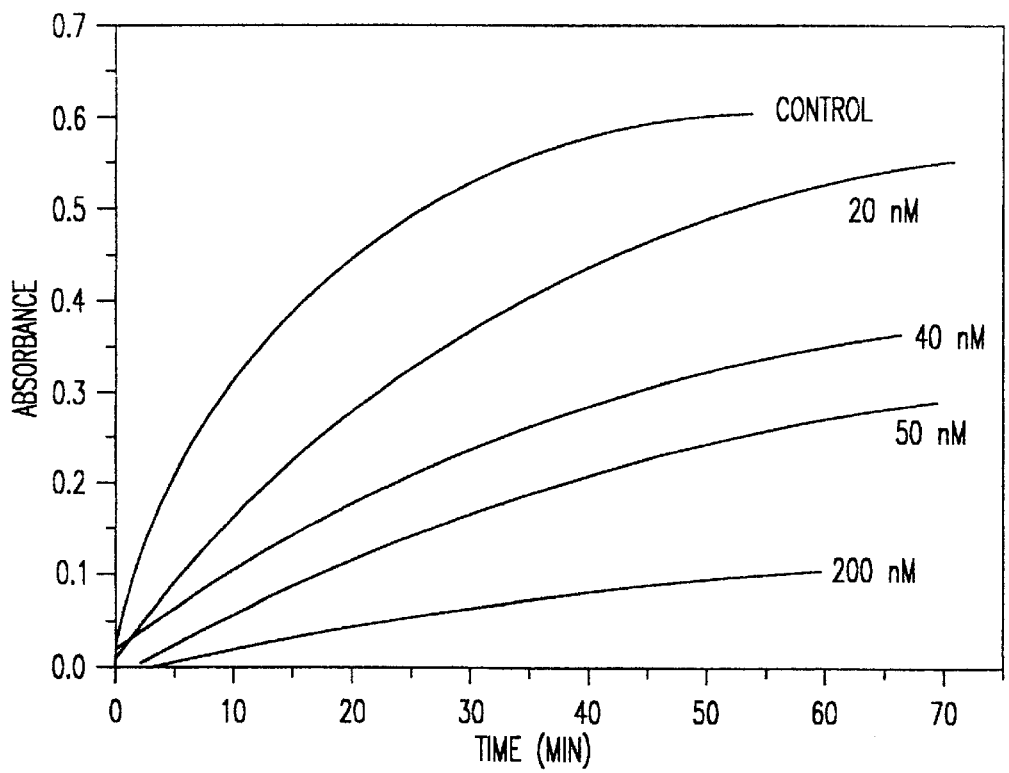

Reaction progress curves for inhibition of human neutrophil elastase (HLE) in the presence of fiber-inhibitor samples were generated (FIG. 1A) and compared to reaction progress curves for inhibition of HLE by the known inhibitor MeOSuc-Val-Pro-Val-chloromethylketone (FIG. 1B). HLE concentrations in the reaction mixtures were 0.5 and 0.2 units/ml for the fiber-inhibitor and the MeOSuc-Val-Pro-Val-chloromethylketone studies, respectively. The weights of the cotton-bound inhibitor samples employed in the inhibition study were in the low milligram range (0.5 to 3.0 mg). The results show that the cotton samples effected a 0.01–0.7 µM inhibitor concentration, as determined by a comparison to inhibition by MeOSuc-Val-Pro-Valchloromethylketone. Further, a dose response relation of enzyme inhibition was demonstrated in the reaction progress curve for the cotton fiber-inhibitor samples.

The dose response of inhibition for HLE was apparent from the linear relation of a plot of reciprocal initial velocities ($1/v_0$) versus weight of fiber-inhibitor. It was likewise apparent that the dose response of inhibition for HLE using freely dissolved inhibitor is within a similar concentration range to that expected for release of inhibitor from the fiber into solution. Thus, the initial velocities ($v_0$) for the weighed fiber-inhibitor samples were within a comparable range to those observed for freely dissolved inhibitor concentrations assayed separately.

Biphasic reaction progress curves were observed for HLE by the free peptide chloromethyl ketone (CMK) and with peptide bound to fiber. This is also indicative of a slow-binding inhibitor. The reaction progress curves for slow-binding inhibitors may be described by the expression of equation 1:

$$P = v_s t + (v_o - v_s)[1 - exp(-k_{obs})/k_{obs} + d$$

Values for $k_{obs}$ were derived from this equation by applying it to the reaction progress curves of HLE. The $k_{obs}$ values for the pre-incubation experiments of fiber-bound and freely dissolved inhibitor with enzyme were generated. The $k_{obs}$ for fiber-bound inhibition (Table 2) of HLE demonstrate the same range and rate decrease as freely dissolved inhibitor.

TABLE 2

Comparison of the $k_{obs}$ for Free and Bound HLE Inhibitors

| Free Inhibitor | | Fiber Bound Inhibitor | |
|---|---|---|---|
| [Inhibitor] $\mu$M | $k_{obs}$ (min$^{-1}$) | Fiber mass (mg) | $k_{obs}$ (min$^{-1}$) |
| Control | 0.087 | | |
| 0.020 | 0.037 | 0.5 | 0.0042 |
| 0.040 | 0.057 | 1.0 | 0.0046 |
| 0.050 | 0.013 | 2.0 | 0.042 |
| 0.2 | 0.003 | 3.0 | 0.638 |

Measurement of Enzyme Inhibition and Wound Fluid Activities

Inhibitory activities were measured by comparing $I_{50}$ values for the inhibitor bound and freely dissolved CMK inhibitor from each of the reaction progress curves. $I_{50}$ reflects the inhibitor concentration or fiber-inhibitor weight in suspension at 50% inhibition using the control inhibitor-free reaction as a benchmark of 100% activity. $I_{50}$ values were assigned for the inhibition of HLE based on a plot of initial rate versus freely dissolved inhibitor and fiber-inhibitor concentration. For HLE the plot of initial rate versus free inhibitor concentration revealed an $I_{50}$ of approximately 11 nM free inhibitor and 0.6 mg of fiber-inhibitor as compared with 29 nM of free inhibitor (based on a semi-quantitative RPHPLC determination) released by 0.6 mg of fiber-inhibitor.

Figure 2A:
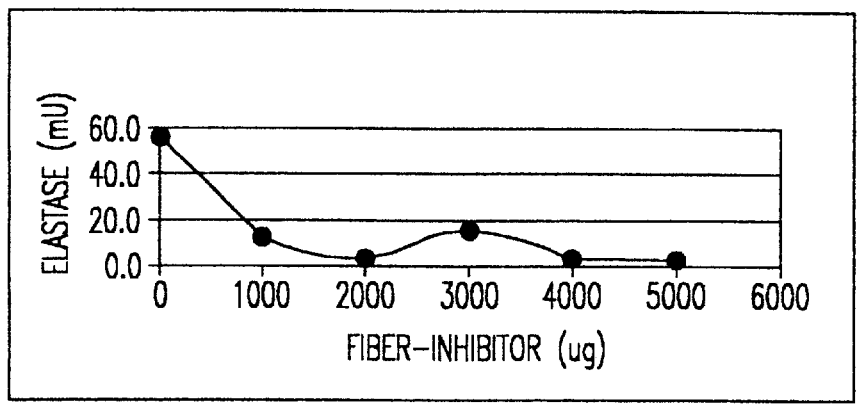
FIGS. 2A–C. Dose response relations for fiber-inhibitor in elastase-containing would fluid. Residual elastase activity in wound fluid after exposure to increasing quantities fiber-inhibitor was measured. Measurements were carried out after 5 (FIG. 2A), 15 (FIG. 2B) and 60 (FIG. 2C) minutes of incubation of the wound fluid with the indicated quantities of fiber-inhibitor. Data is absorbance at 410 nm resulting from catalysis of substrate N-methoxysuccinyl-Ala-Ala-Pro-Val-p-nitroanilide by residual HLE in the samples.
Figure 2B:
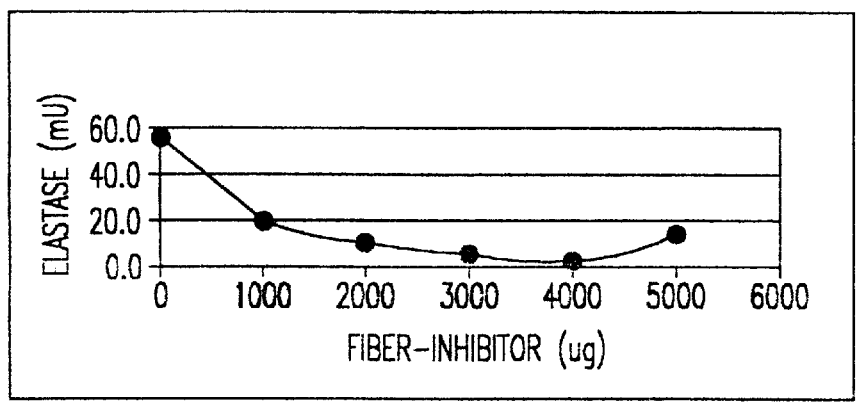
Figure 2C:
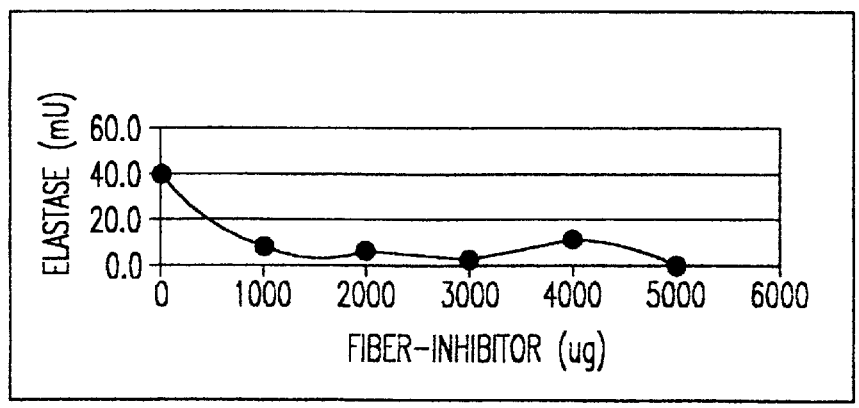

Assessment of the fiber-inhibitor on elastase activity in wound fluid was performed by measuring substrate hydrolysis at fixed time points following incubation of fiber-inhibitor with HLE-containing wound fluid. A dose response of inhibition was evident when fiber-inhibitor samples ranging from 1 mg to 5 mg were incubated in the presence of wound fluid. Elastase activity levels decrease from 40–60 mU in the absence of inhibitor to 0 to 10 mU in the presence of 1 to 5 mg of fiber inhibitor (FIGS. 2A–C).

This decrease in elastase activity with increasing fiber weight demonstrates the inhibitory activity of the serine protease inhibitor as it is released into wound fluid.

The results shown in this Example demonstrate that protease inhibitors which are attached to a cellulose support via a hydrolyzable linkage are capable of effecting the inhibition of a protease in wound fluid.

Example 3
Carboxymethylated and Dialdehyde Cotton Gauze
Methods
Preparation of Dialdehyde Cotton Gauze Dialdehyde cotton gauze (also referred to as 2,3 dialdehyde-anhydroglucos-cellulose, oxidized cellulose, oxycellulose, or periodate-oxidized cellulose) was prepared as follows: cotton gauze (12 ply-4 in.×4 in.), USP type VII, were treated under three different reaction conditions in lots of 50 gauze sponges as follows: Treatment 1: a 0.07 M solution of sodium periodate for 1 h at 45° C. with a solution pH of 4.2. Treatment 2: a 0.2 M solution of sodium periodate for 1.5 h at 45° C. with a solution pH of 4.5. Treatment 3: a 0.2 M solution of sodium periodate for 3 h at 45° C. with a solution pH of 4.5. Following the treatment excess periodate was removed by rinsing the gauze through a screen under running tap water. Following the rinse cycle the gauze samples were passed through a conventional ringer to remove excess moisture. The samples were then separated and placed on a wire rack to air dry overnight. The dried gauzes were placed in Chex all II™ instant sealing pouches (5 in.×10 in.) and sterilized with ethylene oxide gas by Micro Test Laboratories, Agauam, Mass.

Preparation of Carboxymethylated Cotton Gauze

Carboxymethylation was completed as outlined previously (Liyanage et al, 1995). A solution was made by mixing 24 parts of dichloroacetic acid with 24 parts of water, and while cooling in an ice bath, stirring in 75 parts of sodium hydroxide solution. This solution was used to pad a sample of cotton gauze to a wet pickup of 135%. The wet sample was then placed in an oven at 100° C. and dried/cured for 10 minutes.

Determination of Dialdehyde Content and Degree of Substitution of Carboxymethylcellulose Previously outlined procedures were employed to determine the dialdehyde content (Hofreiter et al. 1995) and the degree of substitution for the carboxymethylated gauze (Reinhardt et al.)

Assay of Treated Gauze for Elastase Activity

Treated and untreated gauze samples were submerged in 1 milliliter of buffer containing 0.1 units/ml of human neutrophil elastase. The samples were allowed to incubate for one hour at room temperature, and the gauze samples were removed and placed in a press to drain unbound buffer and enzyme. The unbound buffer and enzyme fractions were combined and assayed for elastase activity as described below.

Enzyme Assays

Enzyme assays of the solutions containing unbound human neutrophil elastase were conducted in pH 7.6 buffer composed of 0.1M sodium phosphate, 0.5 M NaCl, and 3.3% DMSO and subjected to spectrophotometric measurement of the release of p-nitroaniline at 410 nm from the enzymatic hydrolysis of MeOSuc-Ala-Ala-Pro-Val-pNA (Sigma). The spectrophotometric kinetic assays were performed in a BioRad Microplate Reader (Hercules, Calif.) with a 96-well format. 200 microliter aliquots of a elatase solution (0.2 units) were assayed to initiate the enzyme reaction.

Results

The gauze finishes employed in this study were prepared to assess the effect of 1) both sterilization and variation of the sodium periodate finishing conditions on the activity of dialdehyde cotton gauze in reducing elastase activity; and 2) the effect of the degree of substitution of carboxymethylated gauze in reducing elastase activity.

Figure 3:
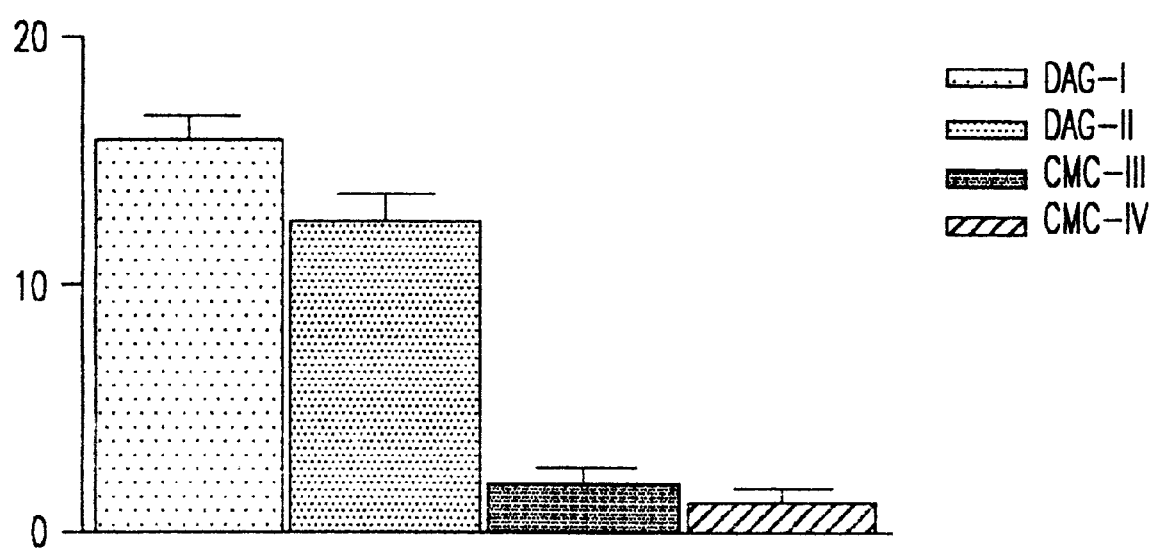
FIG. 3. Percent levels of dicarbonyls in dialdehyde cotton gauze (DAG I and II) and carboxylates on carboxymethylated cellulose (CMC III and IV) as determined by titration of modified cotton fibers. Data are mean ±S.D. of triplicate determinations.

FIG. 3 shows that percent levels of dicarbonyls in two samples of dialdehyde cotton gauze (DAG I and DAG II) on periodate finished cotton ranged from about 12 to 16%. As can be seen, the percent levels of carboxylates on carboxymethylated cellulose samples CMC III and IV were relatively low (approximately 1–2%).

Figure 4A:
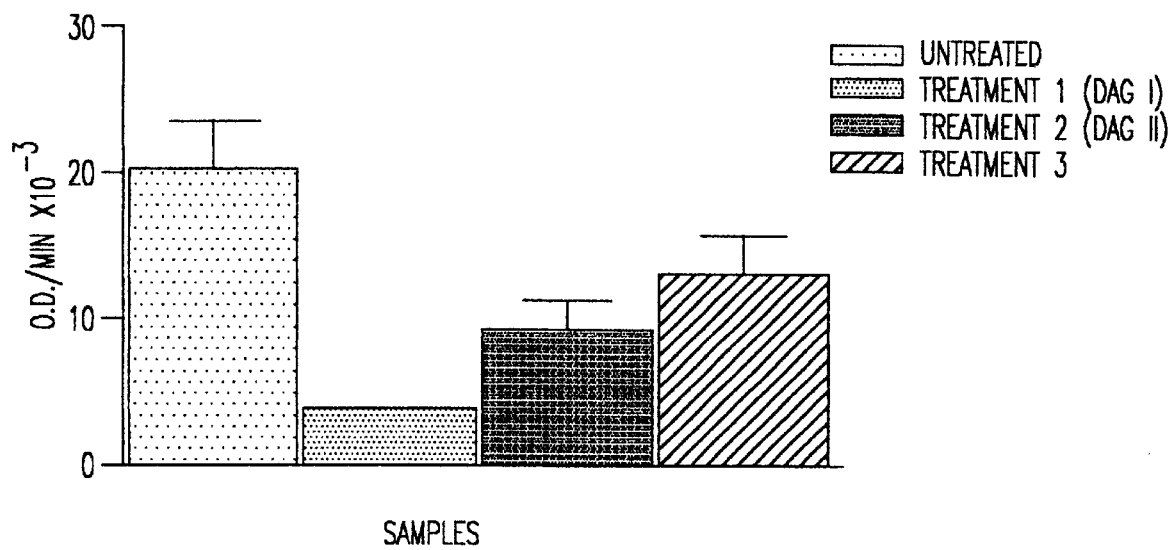
FIGS. 4A and 4B. Assessment of reduction in human neutrophil elastase activity in samples of HLE after exposure to modified cotton gauze. 3A: HLE samples were exposed to three different oxidized cotton gauze samples corresponding to gauze Treatment Methods 1, 2 and 3 (see Methods, Preparation of Dialdehyde Cotton Gauze). 3B: HLE samples were exposed to 25 and 50 mg of two different carboxymethylated cotton gauze samples, III and IV (see Methods, Preparation of Carboxymethylated Cotton Gauze). Untreated gauze was employed as a control. Data are mean ±S.D. of triplicate determinations.

As shown in FIG. 4A, variation of the oxidation conditions, and hence percent aldehyde incorporation, effects elastase-lowering activity of the dialdehyde cotton gauze. The results of these studies suggests that Treatment #1 (see "Preparation of Dialdehyde Cotton Gauze" under Methods above) is optimal for retaining efficacy of the dialdehyde cotton gauze. Prolonged exposure and higher periodate concentration, which is correlated with fewer dicarbonyl units in the cotton cellulose, appears to decrease the efficacy of the gauze in reducing elastase activity in solution.

Figure 4B:
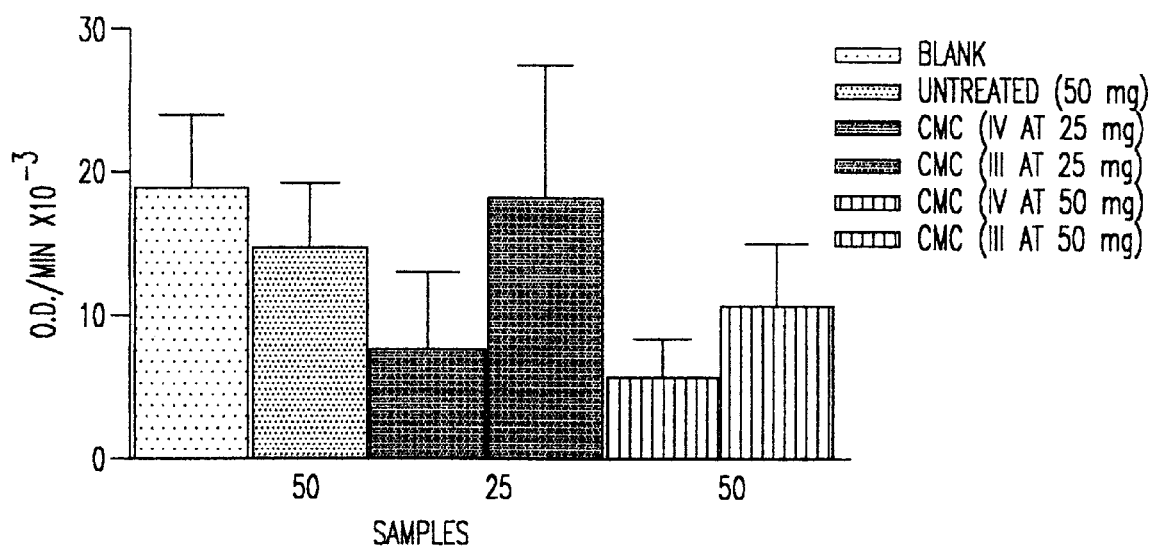

Two different degree of substitution (DS) levels of carboxy methylated cotton cellulose were also compared. As shown in FIG. 4B, higher substitution levels of carboxylate on cotton resulted in an increased reduction in elastase activity in solution.

Correlation of decreased enzyme activity with number of carboxylate or aldehyde sites on cellulose observed within a narrow range of enzyme rates of activity suggests that the cotton derivatized aldehyde and carboxylates bind elastase into readily accessible binding sites in the modified cotton fiber of the gauze.

These results suggest that dialdehyde cotton gauze and carboxymethylated gauze can be used to effect the sequestration of the protease elastase from solutions of the enzyme.

Example 4

Oxidized, Sulfonated, and Phosphorylated Cotton Gauze Dressings Selectively Absorb Neutrophil Elasase Activity in Solution Methods Preparation of Periodate-Oxidized, Sulfonated, and Phosphorylated Cotton.

2,3 dialdehyde-anhydroglucos-cellulose (i.e. Periodate Oxidized) Cotton.

Cotton gauze (12 ply-4 in.×4 in.), USP type VII, was treated in lots of 50 gauze sponges in a 0.07 M solution of sodium periodate for 1 h at 45° C. with a solution pH of 4.2. Alternatively, cotton gauze was oxidized with 0.2M sodium metaperiodate (pH 5) at 40° C. for 3 hours. Following the treatment excess periodate was removed by rinsing the gauze through a screen under running tap water. Following the rinse cycle, the gauze were passed through a conventional ringer to remove excess moisture. The samples were then separated and placed on a wire rack to air dry overnight. The dried gauze are placed in a Chex all II™ instant sealing pouch (5×10 in.) and sterilized with ethylene oxide gas by Micro Test Laboratories, Agauam, Mass.

Sulfonated Cotton.

The cotton gauze may be sulfonated by washing the dialdehyde oxycellulose with 5% sodium bisulfite ($NaHSO_3$) under pH 4.5, liquor ratio 1:60 for 3 hours. Excess sodium bisulfite may be removed by rinsing with water under running tap water. Following the rinse cycle the gauze are passed through a conventional ringer to remove excess moisture. The samples are then separated and placed on a wire rack to air dry overnight.

Phosphorylated Cotton.

Phosphorylation of cotton gauze is accomplished by applying inorganic phosphate salt (sodium hexametaphosphate) to cotton gauze in 4–16% composition. Urea is usually included in the formulation on a 2:1 weight ratio of urea to phosphate. All formulations contained 0.1% Triton X-100 as a wetting agent. The cotton gauze is padded to 80–90% wet pickup and then dried at 60° C. The samples are cured at 160° C. for 7 min.

The phosphorylated and sulfonated cotton cellulose D.S. levels were 0.035 and 0.011 respectively, as measured by elemental analysis.

Carboxymethylated Cotton Gauze

Carboxymethylation was completed as outlined previously (Reinhart et al. 1957). A solution was made by mixing 24 parts of dichloroacetic acid with 24 parts of water and while cooling in an ice bath stirring in 75 parts of sodium hydroxide solution. This solution was used to pad a sample of cotton gauze to a wet pickup of 135%. The wet sample was then placed in an oven at 100° C., and dried/cured for 10 minutes.

Free-Swell Absorbency and Wicking Test

A free-swell absorbency test was performed as follows: A 0.5 gram sample of the cotton gauze was placed in 30 mL of a 0.9% by weight aqueous saline solution and left for 5 minutes. The cotton textile was then filtered through a sintered Mark 1 funnel of pore size 100–160 microns and is left for 5 minutes, or until it stops dripping. The water filtered through the funnel was weighed and the weight of water absorbed by the filaments is calculated by subtraction. A wicking test was made by immersing the cotton gauze in deionized water containing foxboro red dye such that the gauze was just touching the water surface. The time required for the dye solution to migrate 1.5 cm on the gauze strip was measured.

Patients and Wound Fluid

Informed consent was obtained for all procedures, and approval was received from the Virginia Commonwealth University Committee on the Conduct of Human Research, in accordance with the 1975 Declaration of Helsinki. Fluids were harvested from a grade III trochanteric pressure ulcer of a patient with spinal cord injury using a sub-atmospheric device (V.A.C.®, KCI, San Antonio, Tex.). Fluids were clarified by centrifugation at 14,000 g for 15 min at 4° C. The protein concentration was determined with the Bio-Rad Protein assay (Richmond, Calif.) with bovine serum albumin as a quantitation standard.

Assay of Wound Fluid

The patient wound fluid was diluted (1:100; wound fluid: buffer; v:v) at a volume of 3 mL with buffer (0.1M sodium phosphate, 0.5 M NaCl, and 3.3% DMSO) and incubated with weighed samples of gauze ranging from 75 mg to 700 mg. The gauze samples were soaked in the wound fluid solutions for one hour whereupon the solutions were filtered from the gauze under pressure applied to the gauss using a Whatman Autovial (0.45 micron PFTE membrane). Recovery of the wound fluid solution from the gauze was judged to be 90%. The wound fluid solution was assayed for elastase activity in a manner similar to the elastase enzyme assay described below. Rates of substrate hydrolysis were measured on a reaction progress curve of absorbance versus time.

Sequestration and Inhibition of Elastase Activity by Finished Cotton Gauze

The effect of a variety of cotton gauze finishes was tested to assess extraction of elastase from solution. Carboxymethylated, sulfonated, phosphorylated, and oxidized cotton gauze were assayed as 50 and 75 milligram samples of type VII cotton gauze (used typically in patients with chronic wounds). Treated and untreated gauze samples were submerged in 1 milliliter of buffer containing 1 unit/mL of human neutrophil elastase. The samples were allowed to incubate for one hour at room temperature, and each individual gauze sample was removed and placed in an Autovial press filter (Whatman,) to extract unbound buffer and enzyme. The filtered fraction of each individual sample was re-combined with solution not taken up by the gauze and assayed for elastase activity.

The modified gauze containing bound elastase was assessed for recoverable enzyme activity by pooling gauze samples and extracting bound elastase with 20% acetic acid solution. Samples of 1–2 grams of modified gauze were soaked in acetic acid solutions, filtered and the solutions lyophilized to dryness. The lyophilized pellet was resuspended in buffer, filtered on a sintered glass filter funnel and the resulting solution was assayed in 200 microliter aliquots. Elastase activities recovered from the gauze were 43 milliunits per gram in untreated gauze and 160 milliunits per gram from dialdehyde cotton gauze.

Enzyme Assays

Enzyme assays of the solutions containing unbound human neutrophil elastase were conducted in pH 7.6 buffer composed of 0.1M sodium phosphate, 0.5 M NaCl, and 3.3% DMSO and subjected to spectrophotomeric measurement of the release of p-nitroaniline at 410 nm from the enzymatic hydrolysis of N-Methoxysuccinyl-Ala-Ala-Pro-Val-p-nitoranilide (Sigma) (Nakajima et al. 1979). The spectrophotometric kinetic assays were performed in a Bio-Rad Microplate Reader (Hercules, Calif.) with a 96-well format.

Two hundred microliter aliquots of an elastase solution (0.2 units) were assayed per well, and 20 microliters of a 60 micromolar substrate solution was added to initate the enzyme reaction.

Inhibition of Elastase Activity with Dialdehyde Starch

Elastase activity was measured in dialdehyde starch solutions. Solutions of dialdehyde starch (Sigma) were prepared in the buffer described above at concentrations of 100 to 0.1 micromolar. The dialdehyde starch solutions were incubated with stirring in Reacti-Vials with 0.2 units/mL of elastase for an hour. The solutions were centrifuged at 1200× g for five minutes and the supernatant was assayed for elastase activity as described above.

Results

Cotton gauze was subjected to phosphorylation, oxidation, and sulfonation. The degree of substitution (D.S.) was determined by a standard degree of substitution relationship for cellulose (based on the percent of total phosphorous and sulfur for the phosphorylated and sulfonated samples). Base titration of free carboxyls was employed to determine D.S. levels on carboxymethylated cotton cellulose (CMC). The phosphorylated and sulfonated cotton cellulose D.S. levels were 0.035 and 0.011 respectively. This corresponds to one phosphate for every 28 anhydroglucose units and one sulfate for every 91 anhydroglucose units. The degree of substitution for the dialdehyde was also 0.011 since the bisulfite addition reaction is utilized to determine D.S. levels for dialdehyde cotton. The degree of substitution for CMC was 1.4.

Effect of Modified Gauzes on Elastase Activity

Initial experiments examined the ability of the modified cotton celluloses to absorb purified neutrophil elastase. Twenty-five, fifty and seventy-five milligram quantities of gauze were soaked to saturation for an hour in one milliliter of buffered solution containing 0.2 units of elastase. Unbound enzyme was removed by filtration followed by pressing under high pressure. The recovery of buffer from the filtration process was found to be 90%.

Figure 5A:
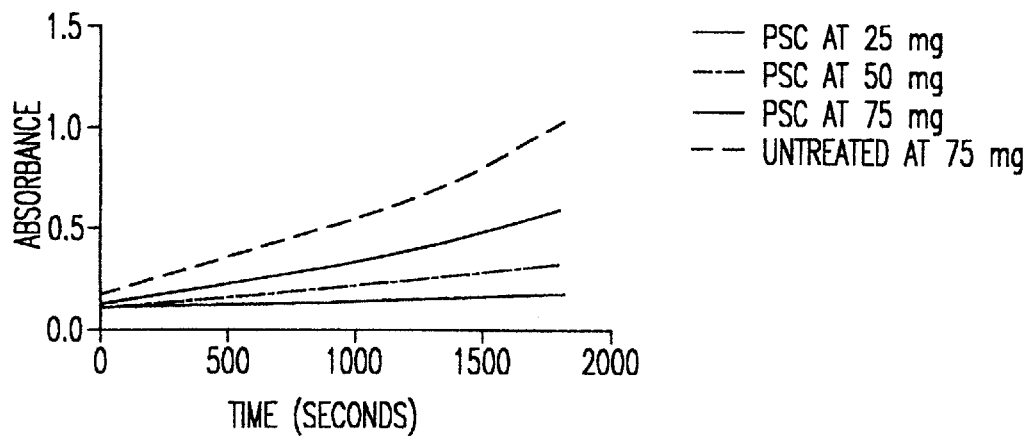
FIGS. 5A–C. Reaction progress curves for gauze-treated solutions of elastase. Substrate hydrolysis was performed with a 60 $\mu$M solution of MeOSuc-Ala-Ala-Pro-Val-pNA and reaction rates monitored by spectrophotometric measurement of the release of p-nitroaniline at 405 nm. 25, 50 and 75 mg samples of phosphorylated cotton gauze (PSC, 5A), sulfonated cotton gauze (SOC, 5B) and dialdehyde cotton gauze (DAG, 5C) were compared with 75 mg of untreated cotton gauze (UT).
Figure 5B:
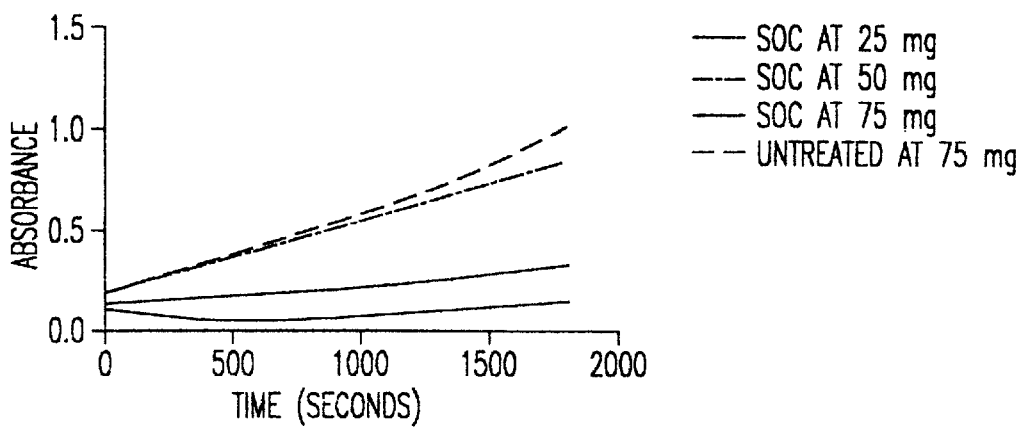
Figure 5C:
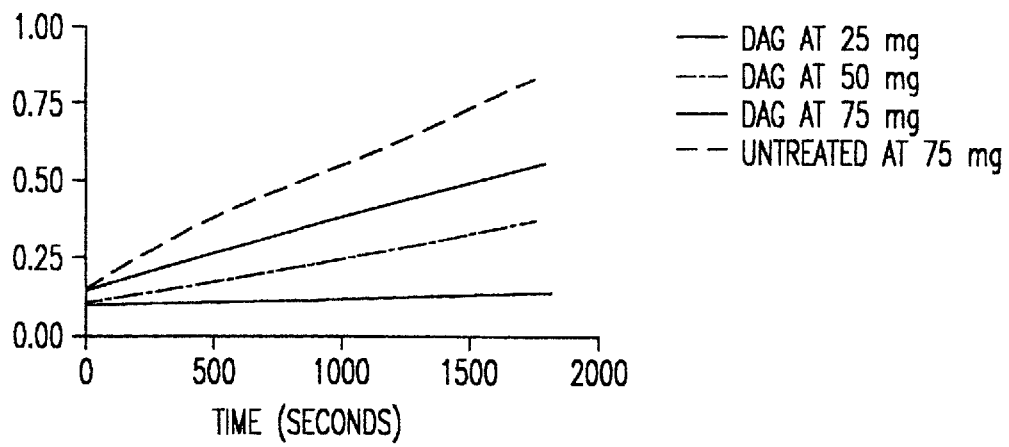
Figure 6:
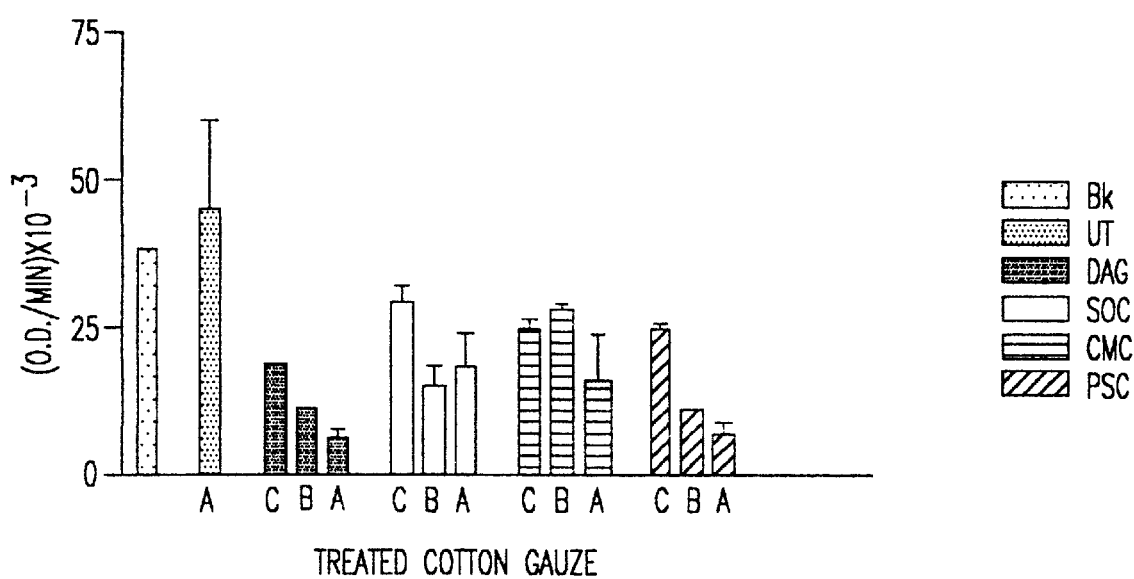
FIG. 6. Initial velocities ($v_0$) of residual elastase activity in samples exposed to untreated gauze (UT), dialdehyde gauze (DAG), sulfonated gauze (SOC), carboxymethylated gauze (CMC) and phosphorylated gauze (PSC), compared to a sample that was not treated with gauze (Bk). Weights of gauze samples were 75 (A), 50 (B), and 25© mg. Data are mean ±S.D. of triplicate determinations. All are significantly different from control, $p<0.05$, as determined by analysis of variance.

The assessment of elastase activity in solution exposed to the treated gauze was performed on the unbound enzyme. Acid-extractable elastase activity was assayed in a 96-well format using MeOSuc-Ala-Ala-Pro-Val-pNa for substrate hydrolysis. The kinetics of elastase activity is based on the relative initial velocity ($v_o$) values for enzyme solutions exposed to cotton gauze. In this study 0.2 units of elastase were tested per sample. Measurement of elastase activity remaining in solution upon treatment with the gauze was accomplished by monitoring the reaction rate within a thirty-minute time frame. The reaction progress curves for the treated samples are shown in FIG. 5. A decrease in active enzyme sites is apparent from the decreasing dose response relation of the treated gauze samples with dialdehyde, sulfonated, and phosphorylated cotton. The decreased rate reflects a decrease in units of elastase activity retained in the eluted buffer. A plot of $v_o$ values shown in FIG. 6 for the samples also demonstrates this dose response relationship. The plot of $v_o$ values was within the same range for the dialdehyde, sulfonated and phosphorylated cotton. A similar decrease in velocity was demonstrated with increasing weight of treated gauze.

The lower $v_o$ values for the treated samples when compared with the untreated cotton gauze suggests that the elastase activity is retained in the treated cotton gauze due to selected modifications on the gauze. Retention of elastase activity in treated gauze was found to be four-fold higher than in untreated gauze.

To assess whether the dialdehyde cotton gauze may act through active site uptake of elastase, dialdehyde starch was employed as a soluble aldehydic polysaccharide that may bind elastase. The results demonstrated that inhibition of elastase by dialdehyde starch is observed within a low micromole range, which is an inhibitory concentration within the titer of aldehydes per gram of dialdehyde cotton used in the current study. Thus, inhibition of elastase activity by a soluble form of a high molecular weight aldehydic carbohydrate suggests that the dialdehyde cotton gauze may function as a serine protease sequestrant through active site access to elastase.

Non-specific binding of the enzyme by the dialdehyde cotton gauze is an alternative explanation for elastase inhibition by dialdehyde cotton gauze. Since aldehydes can form Schiff bases with protein amino groups the potential for Schiff base formation between the protein amino groups of elastase and the aldehydes of dialdehyde cotton (DAG) was a concern. To mimic the effect of protein amines a high molecular weight polylysine was employed. Polylysine is a single amino acid biopolymer containing only epsilon amines as the side chains of the primary amino acid structure. To test for a potential non-specific Schiff base reaction effect between the elastase and the DAG, the dialdehyde cotton was incubated in a polylysine solution and elastase added to the solution to test for retention of elastase-lowering activity. DAG retained its inhibitory effect on elastase in the presence of polylysine. Based on this result it may be inferred that proteinaceous amines do not interfere with the observed elastase-lowering effects of the dialdehyde cotton gauze.

Elastase-Lowering Activity in Wound Fluid

The dialdehyde cotton gauze (DAG) was selected for further evaluation using human wound fluid. To assess the ability of the modified gauze to lower wound fluid-containing elastase activity in comparison to untreated gauze (UT), DAG samples and UT were placed in wound fluid in a range of 2.5 to 20 milligrams of gauze per microliter of patient wound fluid. After exposure to the DAG or UT, the solutions of chronic wound fluid were assessed for residual elastase activity using a known elastase substrate The results showed that the chronic wound fluid which had been exposed to DAG possessed less elastase activity than that which had been exposed to UT at each quantity of guaze tested. This suggests that more elastase has been sequestered by DAG than by UT and is reflected in the initial velocity ($v_o$) values given in Table 3. As can be seen, increasing the quantity of DAG resulted in a dose dependent decrease in the amount of retained elastase activity.

TABLE 3

| Gauze per Volume Fluid mg gauze/ μl Wound Fluid* | UT Gauze Specific Adsorption. (μg protein/ mg gauze) ± S.D.** | UT Gauze $V_0$e-03 ($s^{-1}$) ± S.D.*** | DAG Specific Adsorption. (μg protein/ mg gauze) ± S.D.** | DAG $V_0$e-03 ($s^{-1}$) ± S.D.*** |
|---|---|---|---|---|
| 2.5 | 8.74 ± 0.06 | 2.81 ± 0.068 | 7.42 ± 1.2 | 2.46 ± 0.038 |
| 7.5 | 1.10 ± 0.62 | 1.18 ± 0.047 | 3.49 ± 0.28 | 0.64 ± 0.028 |
| 10.8 | 1.69 ± 0.69 | 0.62 ± 0.129 | 2.82 ± 0.44 | 0.23 ± 0.14 |
| 14.2 | 1.60 ± 0.33 | 0.22 ± 0.057 | 2.69 ± 0.39 | 0.08 ± 0.03 |
| 17.5 | 1.40 ± 0.24 | 1.09 ± 0.137 | 1.83 ± 0.29 | NA**** |

*mg gauze/ul wound fluid (w.f.) was calculated by dividing the gauze mass by the volume of the wound fluid (w.f.) used in the experiment. For example (75 mg gauze/3 ml diluted w.f.) × (1 ml diluted w.f./10 μL (0.01 ml) w.f.) = 2.5 mg gauze/μL w.f. The elastase activity (0.25–.0.27 units) of the wound fluid used in these experiments was the same as shown in FIG. 5B.
**Specific adsorption of protein on gauze (μg protein/mg gauze) was determined by dividing the residual protein mass by the initial gauze mass. Residual protein mass remaining on the gauze after exposure to wound fluid was calculated by subtracting the protein mass remaining in solution from the initial protein mass of the solution diluted 1:100 (wound fluid:buffer, v:v). [Protein] 1:100 solution μg/mL × 3 mL = Initial protein mass;

TABLE 3-continued

| Gauze per Volume Fluid mg gauze/ μl Wound Fluid* | UT Gauze Specific Adsorption. (μg protein/ mg gauze) ± S.D.** | UT Gauze $V_0$e-03 $(s^{-1}) \pm$ S.D.*** | DAG Specific Adsorption. (μg protein/ mg gauze) ± S.D.** | DAG $V_0$e-03 $(s^{-1}) \pm$ S.D.*** |
|---|---|---|---|---|

[Protein] after exposure μg/mL × (3.0 mL × 0.9) = Protein in solution after incubation. Initial protein mass - protein mass after incubation = Gauze-bound (residual protein).
***NA (No measurable rate or elastase activity).
***Reaction rates are reported as initial velocities ($v_0$) which were taken from the slope of the linear least squares fit of absorbance-time data of the reaction progress profiles as described in the Materials and Methods section under Enzyme Assays.

Data are mean ±SD of triplicate determinations. All are significant when compared within the five groups of protein and reaction rate data such that p<0.05 and were determined by one-way ANOVA and analysis of variance.

These results reflect the superior ability of the DAG samples to remove elastase activity from wound fluid as compared to untreated cotton gauze. Dialdehyde cotton gauze extracted 2-5 fold more elastase activity with increased gauze loading per volume of wound fluid when compared with untreated gauze.

Measurement of protein levels remaining in the wound fluid following incubation with the gauzes was performed to compare the relative amounts of protein taken up by treated and untreated gauze. Lower levels of protein were found in the wound fluid soaked with DAG than with the untreated cotton. This is consistent with the lower activity of elastase found in the wound fluid soaked with DAG samples.

The results obtained in this Example demonstrate that dialdehyde cotton effects the sequestration of the protease elasetase from wound fluid.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Allman, R. M. 1998. The impact of pressure ulcers on health care costs and mortality. Adv Wound Care 11:2—2.
Diegelmann, R. F., M. S. Creehan, M. L. Wallace, D. R. Yager, and I. K. Cohen. 1999. Excessive neutrophils and highly activated fibroblasts characterize non-healing pressure ulcers in humans. Third Joint Meeting of the European Tissue Repair Society & Wound Healing Society (Abstract)
Eichler, J., Bievert, M, Sturandova, M. 1991, Evaluation of Cotton as a Carrier for Solid-Phase Peptide Synthesis. *Peptide Res.* 4, 296–307.
Falanga, V., F. Grinnell, B. Gilchrest, Y. T. Maddox, and A. Moshell. 1994. Workshop on the pathogenesis of chronic wounds. J Invest Dermatol 102:125–127.
Hofreiter, B. T., Alexander, B. H. Wolff, I. A. 1955. Anal. Chem. 27: 1930–1931.
Lazarus, G. S., D. M. Cooper, D. R. Knighton, D. J. Margolis, R. E. Pecoraro, G. Rodeheaver, and M. C. Robson. 1994. Definitions and guidelines for assessment of wounds and evaluation of healing. Arch Dermatol 130:489–493.
Liyanage, J. A., Taylor, D. M., Williams, D. R. Chem. Spec. Bioavail. 1995. 7:73–75.
Nakajima, L, Powers, J. C., Ashe, B. M., Zimmerman, M. Mapping the estended substrate binding site of cathepsin G and human leukocyte elastase. J. Biol. Chem. 254, 10, 4027–4032.
Nwomeh, B. C., H. X. Liang, I. K. Cohen, and D. R. Yager. 1998. Dynamics of the matrix metalloproteinases MMP-1 and MMP-8 in acute open human dermal wounds. Wound Repair Regen 6:127–134.
Nwomeh, B. C., H. X. Liang, R. F. Diegelmann, I. K. Cohen, and D. R. Yager. 1999. Matrix metalloproteinase-8 is the predominant collagenase in healing wounds and non-healing ulcers. J Surg Res 81:189–195.
Nwomeh, B. C., D. R. Yager, and I. K. Cohen. 1998. Physiology of the chronic wound. Clin Plast Surg 25:341–356.
Palolahti, M., J. Lauharanta, R. W. Stephens, P. Kuusela, and A. Vaheri. 1993. Proteolytic activity in leg ulcer exudate. Exp Dermatol 2:29–37.
Reinhardt, R. M., Fenner, T. W., and Reid, J. D. Textile res. Journal 27, 11.
Rogers, A. A., S. Burnett, J. C. Moore, P. G. Shakespeare, and W. Y. J. Chen. 1995. Involvement of proteolytic enzymes-plasminogen activators and matrix metalloproteinases-in the pathophysiology of pressure ulcers. Wound Repair Regen 3:273–283.
Weiss, S. J. 1989. Tissue destruction by neutrophils. N Eng J Med 320:365–376.
Williams, J. W. and Morrison, J. F. The kinetics of reversible tight-binding inhibition. Methods in Enzymology, 63, 437–467.
Wysocki, A. B. 1996. Wound fluids and the pathogenesis of chronic wounds. J Wound Ostomy Continence Nurs 23:283–290.
Wysocki, A. B., L. Staiano-Coico, and F. Grinnell. 1993. Wound fluid from chronic leg ulcers contains elevated levels of metalloproteinases MMP-2 and MMP-9. J Invest Dermatol 101:64–68.
Yager, D. R., S. M. Chen, S. I. Ward, O. O. Oluyinka, R. F. Diegelmann, and I. K. Cohen. 1997. Ability of chronic wound fluids to degrade peptide growth factors is associated with increased levels of elastase activity and diminished levels of proteinase inhibitors. Wound Repair Regen 5:23–32.
Yager, D. R., L. Y. Zhang, H. X. Liang, R. F. Diegelmann, and I. K. Cohen. 1996. Wound fluids from human pressure ulcers contain elevated matrix metalloproteinase levels and activity compared to surgical wound fluids. J Invest Dermatol 107:743–748.

We claim:

1. A method for sequestering elastase at a wound site, comprising the step of contacting said wound site with a dialdehyde gauze wound dressing.

2. A method for sequestering elastase at a wound site, comprising the step of contacting said wound site with a sulfonated gauze wound dressing.

3. A method for sequestering elastase at a wound site, comprising the step of contacting said wound site with a phosphorylated gauze wound dressing.

4. A method for sequestering elastase at a wound site, comprising the step of contacting said wound site with a cotton gauze wound dressing selected from the group consisting of a dialdehyde cotton, a sulfonated cotton, or a phosphorylated cotton.

* * * * *